United States Patent [19]

Crissman et al.

[11] Patent Number: 5,084,378
[45] Date of Patent: Jan. 28, 1992

[54] ENHANCED DETECTION OF FLUORESCENCE QUENCHING IN LABELED CELLS

[75] Inventors: Harry A. Crissman; John A. Steinkamp, both of Los Alamos, N. Mex.

[73] Assignee: The United States of America as represented by the United States Department of Energy, Washington, D.C.

[21] Appl. No.: 126,155

[22] Filed: Nov. 30, 1987

[51] Int. Cl.$^5$ .................. C12Q 1/68; G01N 33/48; G01N 33/15; G01N 21/76

[52] U.S. Cl. ........................... 435/6; 436/546; 436/56; 436/63; 436/94; 436/172; 436/800; 424/7.1; 935/77

[58] Field of Search .............. 436/501, 63, 546, 56, 436/94, 172, 800; 435/6; 424/7.1; 935/77

[56] References Cited

U.S. PATENT DOCUMENTS 4,585,736  4/1986  Dolbeare et al. ............... 435/6
4,780,406  10/1988  Dolbeare et al. ............... 435/6
4,812,394  3/1989  Dolbeare et al. ............... 435/6

OTHER PUBLICATIONS

Kubbies et al., Cytometry, vol. 3(4), pp. 276-281 (1983).
Cremer et al., Cytometry, vol. 3(4), pp. 282-286 91983).
Ullman et al., "Homogeneous Fluorescence Immunoassays", in Immunoassays: Clinical Laboratory Techniques for the 1980s, Alan R. Liss, Inc., New York (1980), pp. 13-43.
Cremer et al., Biological Abstracts, vol. 74(11): 75811 (Nov. 1982).
Kubbies et al., Chemical Abstracts, vol. 103: 210250c, (Dec. 1985).
Hamilton et al., Chemical Abstracts, vol. 93: 145776n (Oct. 1980).
Severin et al., Biological Abstracts, vol. 76(2): 10311 (Jul. 1983).
Samuel A. Latt, "Microfluorometric Detection of Deoxyribonucleic Acid Replication in Human Metaphase Chromosomes", Proc. Nat. Acad. Sci. USA 70 No. 12, pp. 3395-3399 (Dec. 1973).
J. A. Steinkamp et al., "Dual-Laser, Differential Fluorscence Correction Method for Reducing Cellular Background Autofluoroescence", Cytometry 7, p. 566 (1986).

Primary Examiner—Esther L. Kepplinger
Assistant Examiner—Janelle Graeter
Attorney, Agent, or Firm—Ray G. Wilson; Paul D. Gaetjens; William R. Moser

[57] ABSTRACT

A method is provided for quantifying BrdU labeled DNA in cells. The BrdU is incorporated into the DNA and the DNA is stained with a first fluorochrome having a fluorescence which is quenchable by BrdU. The first fluorochrome is preferably a thymidine base halogen analogue, such as a Hoechst fluorochrome. The DNA is then stained with a second fluorochrome having a fluorescence that is substantially uneffected by BrdU. The second fluorochrome may be selected from the group consisting of mithramycin, chromomycin A3, olivomycin, propidium iodide and ethidium bromine. The fluorescence from the first and second fluorochromes is then measured to obtain first and second output signals, respectively. The first output signal is substracted from the second output signal to obtain a difference signal which is functionally related to the quantity of BrdU incorporated into DNA. The technique is particularly useful for quantifying the synthesis of DNA during the S-phase of the cell cycle.

19 Claims, 2 Drawing Sheets

ENHANCED DETECTION OF FLUORESCENCE QUENCHING IN LABELED CELLS

This invention relates to flow cytometry and, more particularly, to flow cytometry detection and quantitation using fluorescence quenching of fluorochromes in bromodeoxyuridine (BrdU) labeled cells. This invention is the result of a contract with the Department of Energy (Contract No. W-7405-ENG-36).

BACKGROUND OF THE INVENTION

Studies on cell cycle traverse, DNA synthesis, and cell proliferation have been significantly advanced through the use of labeled DNA precursors. More recently, nonradioactive molecules, such as the base analoque 5 BrdU, have been substituted for radio-labeled DNA precursors. BrdU is substituted stoichiometrically for thymidine in DNA during the S-phase (synthesis) of cell growth where the cellular DNA content is doubling between the $G_1$ and $G_2$ cell phases. A measure of the incorporated BrdU is related to the new DNA content, i.e., the status or location of the cell in the S-phase.

Thus, the detection of BrdU-substituted DNA is functionally related to synthesis of DNA during the S-phase of the cell cycle. One detection technique employs an immunofluorescent assay of BrdU. This technique requires the partial denaturation of cellular DNA by heat or acid treatment to expose the incorporated BrdU to the antibody. In a variation of the procedure, a fluorescent counterstain, propidium iodide (PI), is included to measure the total DNA content. Using two-color, flow cytometric analysis, cells containing incorporated BrdU are readily detected and their cell cycle position is easily assessed.

Another method for detecting BrdU-substituted DNA uses the A-T base binding fluorochrome, Hoechst 33258, that is quenched when bound to A-BrdU regions in double-stranded DNA. This effect is described in Samuel A. Latt, "Microfluorometric Detection of Deoxyribonucleic Acid Replication in Human Metaphase Chromosomes," Proc. Nat. Acad. Sci. USA 70 No. 12, p. 3395-3399 (December 1973). The BrdU/Hoechst fluorescence quenching technique, however, is not as sensitive as the immunofluorescent assay. There is difficulty in assessing quantitatively the reduction of Hoechst fluorescence after short exposure periods to BrdU, e.g., 30 minutes. BrdU exposure periods of six hours or longer were required for cells to incorporate sufficient amounts of BrdU for assessing Hoechst quenching.

The present invention overcomes the problems of resolution and sensitivity with conventional Hoechst quenching processes and an improved process is provided for detecting BrdU/Hoechst fluorescence quenching.

Accordingly, one object of the present invention is to provide a sensitive technique for enhancing the detection of Hoechst quenching in labeled DNA.

Another object of the present invention is to enable the quantitation of BrdU during cell S-phase growth.

One other object of the present invention is to provide an assay process for BrdU which minimizes cell loss and damage to cellular markers in DNA, RNA, and/or chromatin.

SUMMARY OF THE INVENTION

To achieve the foregoing and other objects, and in accordance with the purposes of the present invention, as embodied and broadly described herein, the process of this invention may comprise quantifying BrdU-labeled DNA in cells by incorporating BrdU into DNA being investigated, staining the DNA with a first fluorochrome having a fluorescence which is quenchable by BrdU, and then staining the DNA with a second fluorochrome having a fluorescence which is substantially unaffected by BrdU. The fluorescence from the first and second fluorochromes is then measured to obtain first and second output signals, respectively. The first output signal is subtracted from the second output signal to obtain a difference signal which is functionally related to the quantity of incorporated BrdU. Bivariate contour profiles produced from the output signals show significant differentiation between S-phase cells and $G_1$ and $G_2 + M$-phase cells.

In another characterization of the present invention, a method is provided for quantifying labeled DNA in cells The DNA is labeled with a thymidine base halogen analogue. The DNA is then stained with a Hoechst fluorochrome having a fluorescence which is quenchable by the analogue and a second fluorochrome which is substantially unaffected by the analogue. The fluorescence from the Hoechst and the second fluorochrome is then measured to obtain first and second output signals, respectively. A difference signal is obtained which is fuctionally related to the quantity of the halogen analogue incorporated in the cellular DNA.

In one other characterization of the present invention, a solution is provided for enhancing the detection of BrdU incorporated into cellular DNA. A first fluorochrome is selected which is quenchable by BrdU and a second fluorochrome is provided which is unaffected by BrdU.

BRIEF DESCRIPTION OF THE DRAWINGS

The accompanying drawings, which are incorporated in and form a part of the specification, illustrate the embodiment of the present invention and, together with the description, serve to explain the principles of the invention. In the drawings.

DETAILED DESCRIPTION

Figure 1:
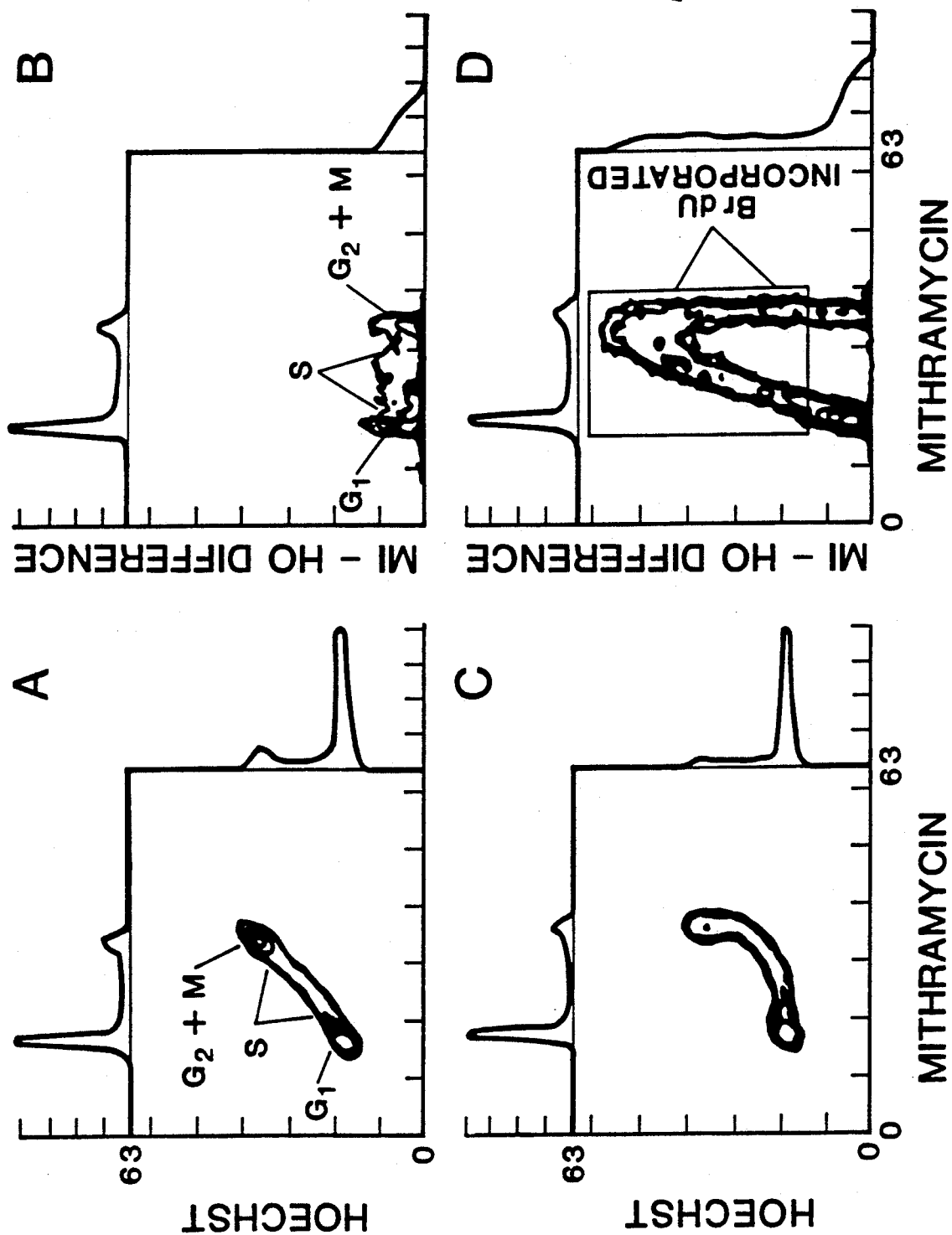
FIG. 1A is a frequency distribution histogram and a corresponding bivariate contour diagram constructed from output signals for Hoechst fluorochrome and a mithramycin fluorochrome, with no BrdU incorporation.
FIG. 1B is a representation similar to FIG. 1A depicting a difference signal amplitude.
FIG. 1C is a representation similar to FIG. 1A where the cells have been treated in culture with BrdU.
FIG. 1D is a representation similar to FIG. 1A using a difference signal amplitude to show the sensitivity of the present invention to differentiate S-phase cells.

In accordance with the present invention a new flow cytometric technique, involving differential fluorescence analysis of two DNA-binding fluorochromes, is used to quantify cellular incorporation of a base analogue, such as BrdU, into DNA over short time periods. A first fluorochrome is provided with a fluorescence that is quenched by the incorporated BrdU. A second fluorochrome is provided which is unaffected by BrdU. By differencing the output amplitudes of the two fluorescence signals on a cell-by-cell basis an output signal is obtained which is generally proportional to the incorporated BrdU quantity.

In one embodiment of the invention, cells with BrdU-substituted DNA are stained with a first fluorochrome, such as Hoechst 33342, having a fluorescence which is quenched by BrdU-substituted DNA, and a second fluorochrome, such as mithramycin (MI), which is not affected by the BrdU. The quenched blue fluorescence signal of Hoechst 33342 is subtracted, on a cell-by-cell basis, from the green-yellow fluorescence signal of MI. Bivariate contour profiles obtained for cells labeled with BrdU show that fluorescence quenching of Hoechst 33342 in BrdU labeled, S-phase cells, produces fluorescence difference signals that are significantly greater than the difference signals from $G_1$ and $G_2+M$-phase cells. The process is relatively simple, rapid, and mild, producing minimal cell loss and without effecting cellular moeities such as DNA, chromatin, or RNA.

In accordance with one embodiment of the present invention, the technique uses two nonintercalating, DNA-specific fluorochromes: A-T binding Hoechst 33342 (HO) and G-C binding, mithramycin (MI), a dye whose fluorescence in the presence of BrdU remains stoichiometric to DNA content. Using dual-wavelength excitation, the blue HO and green-yellow MI fluorescence emissions are measured and a differential amplifier subtracts the blue fluorescence from the green-yellow fluorescence signal amplitude on a cell-by-cell basis. Cells in S-phase exhibit a significant BrdU/Hoechst quenching and produce a greater differential fluorescence signal, compared to cells in the $G_1$ and $G_2+M$ phase, which generally show relatively small fluorescence differences.

EXAMPLE 1

Chinese hamster cells (line CHO) were maintained in exponential growth phase in suspension culture free of mycoplasma contamination in Ham's F-10 medium supplemented with heat-activated newborn calf serum (15%), penicillin (100 U/ml), and streptomycin (100 µg/ml). Cell cycle generation time was approximately 15-16 hours. Populations of cells were treated in the dark with 30 µM BrdU (Sigma Chem. Co.) for 30 minutes prior to fixation, staining, and analysis. The BrdU concentration has no affect on the cell cycle frequency distribution or on cell proliferation of CHO cells treated for at least 24 hours.

EXAMPLE 2

Suspension cultures of L1210 cells (American Type Culture) were maintained in exponential growth phase in minimum essential medium-alpha containing 15% fetal calf serum. Population doubling time was about 10-11 hours. BrdU was added to cultures to a final concentration of 10 µM, without adverse effects. At various time intervals, cells were removed from culture, rapidly chilled and fixed in 70% ethanol. Cells fixed in 70% ethanol, for 1 hour up to 1 week, were subsequently stained for at least 1 hour in phosphate-buffered saline containing 0.5 µg/ml Hoechst 33342, 5.0 µg/ml mithramycin, and 5.0 mM $MgCl_2$ prior to analysis in a dual laser flow cytometer. A total of $2.5 \times 10^4$ cells were analyzed from each population using the uv (0.5 W) and the 457 nm (0.2 W) wavelength lines from argon lasers to excite and measure the HO and MI fluorescence.

The HO fluorescence signal was subtracted from the MI fluorescence signal on a cell-by-cell basis using an analogue subtraction circuit, described by J. A. Steinkamp et al., "Dual-Laser, Differential Fluorescence Correction Method for Reducing Cellular Background Autofluorescence," Cytometry 7, p. 566 (1986).

Referring now to FIG. 1A, there is shown a DNA content (HO and MI) frequency distribution histogram and the corresponding bivariate contour diagram for untreated CHO cells. The X and Y axes are linear relative units. It can be seen that the cells show an equal affinity for both HO and MI dyes as seen by the linear relationship and staining throughout the cell cycle.

FIG. 1B provides the signal difference frequency distribution for the untreated cells. FIG. 1C illustrates the effect of BrdU treatment as set out in Example 1 on the HO and MI histogram. The cell population treated for 30 minutes with 30 µM BrdU shows a significant quenching of HO fluorescence in S-phase, while the $G_1$ and $G_2+M$ subpopulations are essentially unaffected. A comparison of FIGS. 1A and 1C indicate that MI fluorescence was not affected by BrdU-substituted DNA, nor by the quenching of the Hoechst fluorescence.

Referring now to FIG. 1D, the significance of the process according to the present invention is illustrated. The magnitude of the fluorescence differences (MI minus HO), reflecting BrdU/Hoechst quenching, is most significant for cells in S-phase that have incorporated BrdU. The percentage of S-phase cells containing BrdU detected by the present technique is in good agreement with the percentage derived by standard autoradiography.

Figure 2:
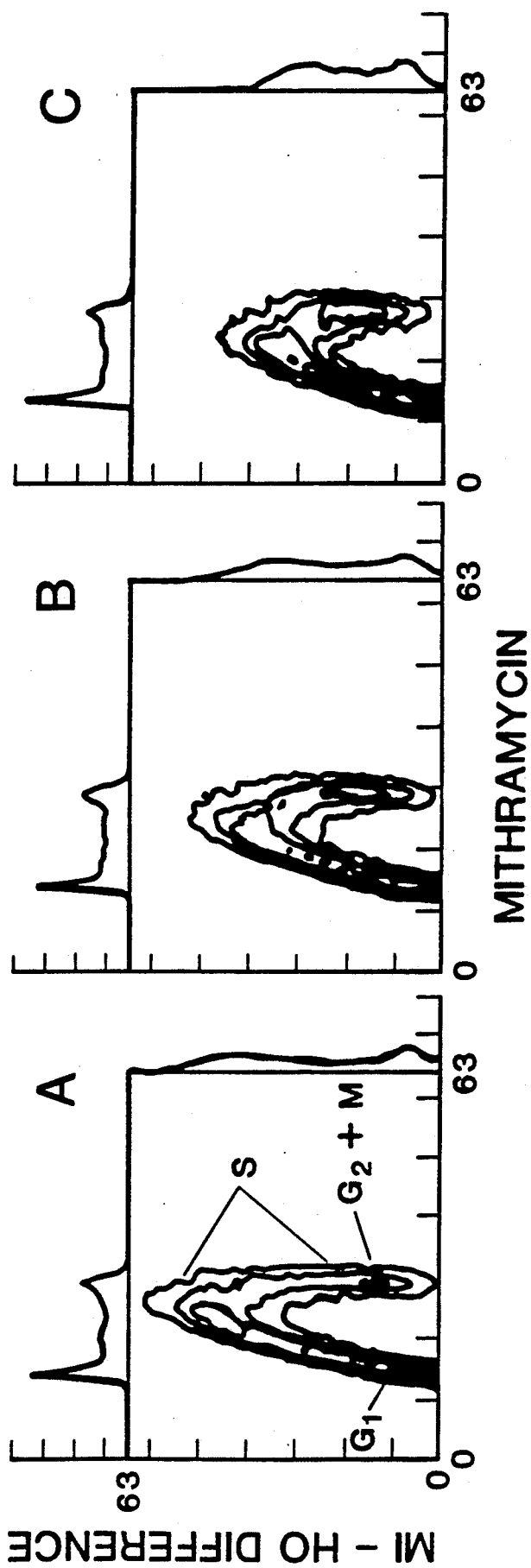
FIGS. 2A, 2B, 2C are frequency distribution histograms and corresponding bivariate contour diagrams to show the sensitivity of the process with cells exposed to BrdU for time periods of 30, 15, and 5 minutes, respectively.

The sensitivity and stoichiometry of the technique were examined using the L1210 cells and culture prepared in accordance with Example 2. FIGS. 2A, 2B, and 2C show that the amount of BrdU detected by the differential fluorescence measurement was proportional to the period of BrdU labeling. Cells in the S-phase with incorporated BrdU are clearly separated from the $G_1$ and $G_2+M$ subpopulations for the exposure times of 30, 15, and 5 minute durations, respectively. Thus, the subject procedure can be rapidly applied with only a mild treatment for the cell cultures.

It will be appreciated that the above results are not limited to BrdU, Hoechst 33342 and mithramycin fluorochromes. Compounds other than BrdU also exhibit quenching of Hoechst fluorochromes. BrdU is a thymidine base bromine analogue, but any halogen substitution will provide a suitable quenching compound, i.e., a thymidine base halogen analogue. The Hoechst fluorochrome, generally 2-[2-(4-hydroxyphenyl)-6-benzimida- zolyl]-6-(1- methyl-4-piperazyl)-benzimidazole . 3 HCl, and particularly Hoechst 33342 or 33258, is a preferred first fluorochrome, but any fluorochrome which exhibits fluorescence quenching with a thymidine base halogen analogue may be used.

Likewise, the second fluorochrome, which is not effected by the halogen analogue substitution, may be selected from fluorochromes which are DNA specific and provide a fluorescence which is proportional to the DNA content of the cells. A suitable fluorochrome may be selected from chromomycin A3, olivomycin, propidium iodide or ethidium bromine.

The use of MI or a related compound does provide some particular advantages for fluorescence difference analysis of BrdU-labeled cells. It has been shown that the exposure of CHO cells to BrdU for one cell cycle generation enhanced MI fluorescence of the entire population by 25%. This may be due to BrdU induced alterations in native chromatin configuration which increased the availability of MI binding sites. This phenomenon tends to further enhance the sensitivity of the MI-HO differential fluorescence measurements, since the increase in MI fluorescence would occur concomitant with the decrease in HO fluorescence.

The foregoing description of the preferred embodiment of the invention has been presented for purposes of illustration and description. It is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for relatively quantifying BrdU-labeled DNA in cells in an S-phase during a selected interval within a cell cycle, comprising the steps of:
    incorporating said BrdU into said DNA for a time of about 5 minutes to thirty minutes;
    staining said DNA with a first fluorochrome having a fluorescence which is quenchable by BrdU;
    staining said DNA with a second fluorochrome having a fluorescence which is substantially unaffected by BrdU;
    measuring fluorescence from said first and second fluorochromes to obtain first and second output signals, respectively, on a cell-by-cell basis; and
    subtracting said first output signal from said second output signal to obtain a different signal functionally related to the quantity of incorporated BrdU.

2. A method according to claim 1, wherein said first fluorochrome attaches to A and T bases of said DNA.

3. A method according to claim 2, wherein said fluorochrome is a Hoechst dye.

4. A method according to claim 1, wherein said second fluorochrome is DNA specific with a fluorescence output intensity proportional to DNA content of said cells.

5. A method according to claim 2, wherein said second fluorochrome is DNA specific with a fluorescence output intensity proportional to DNA content of said cells.

6. A method according to claim 3, wherein said second fluorochrome is DNA specific with a fluorescence output intensity proportional to DNA content of said cells.

7. A method according to claim 1, wherein said second fluorochrome is selected from the group consisting of mithramycin, chromomycin A3, olivomycin, propidium iodide, and ethidium bromide.

8. A method according to claim 1, wherein said second fluorochrome is mithramycin.

9. A method according to claim 2, wherein said second fluorochrome is selected from the group consisting of mithramycin, chromomycin A3, olivomycin, propidium iodide, and ethidium bromide.

10. A method according to claim 3, wherein said second fluorochrome is selected from the group consisting of mithramycin, chromomycin A3, olivomycin, propidium iodide, and ethidium bromide.

11. A method according to claim 4, wherein said second fluorochrome is selected from the group consisting of mithramycin, chromomycin A3, olivomycin, propidium iodide, and ethidium bromide.

12. A method according to claim 2, wherein said second fluorochrome is mithramycin.

13. A method according to claim 3, wherein said second fluorochrome is mithramycin.

14. A method according to claim 4, wherein said second fluorochrome is mithramycin.

15. A method for relatively quantifying labeled DNA in cells in an S-phase during a selected interval within a cell cycle, comprising the steps of:
    labeling said DNA with a thymidine base halogen analogue for a time of about 5 minutes to thirty minutes;
    staining said DNA with a Hoechst fluorochrome having a fluorescence which is quenchable by said analogue;
    staining said DNA with a second fluorochrome having a fluorescence which is substantially unaffected by said analogue;
    measuring fluorescence from said first and second fluorochromes to obtain first and second output signals, respectively; and
    subtracting said first output signal from said second output signal to obtain a difference signal functionally related to the quantity of said incorporated halogen analogue.

16. A method according to claim 15, wherein said second fluorochrome is DNA specific with a fluorescence output intensity proportional to DNA content of said cells.

17. A method according to claim 15, wherein said second fluorochrome is selected from the group consisting of mithramycin, chromomycin A3, olivomycin, propidium iodide, and ethidium bromide.

18. A method according to claim 15, wherein said second fluorochrome is mithramycin.

19. A method according to claim 16, wherein said second fluorochrome is selected from the group consisting of mithramycin, chromomycin A3, olivomycin, propidium iodide, and ethidium bromide.

* * * * *